(12) United States Patent
Wietelmann et al.

(10) Patent No.: US 6,506,516 B1
(45) Date of Patent: Jan. 14, 2003

(54) LITHIUM BISOXALATOBORATE, THE PRODUCTION THEREOF AND ITS USE AS A CONDUCTING SALT

(75) Inventors: Ulrich Wietelmann, Friedrichsdorf (DE); Uwe Lischka, Frankfurt am Main (DE); Marion Wegner, Frankfurt am Main (DE)

(73) Assignee: Metallgesellschaft Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 09/720,656
(22) PCT Filed: Jun. 7, 1999
(86) PCT No.: PCT/EP99/03908
§ 371 (c)(1),
(2), (4) Date: Mar. 9, 2001
(87) PCT Pub. No.: WO00/00495
PCT Pub. Date: Jan. 6, 2000

(30) Foreign Application Priority Data

Jun. 30, 1998 (DE) .......................... 198 29 030

(51) Int. Cl.$^7$ ............................ C01B 35/10; H01M 6/04
(52) U.S. Cl. ...................................... 429/188; 423/277
(58) Field of Search ................................ 423/277, 592, 423/179.5, 202; 429/188

(56) References Cited

FOREIGN PATENT DOCUMENTS

DE          19633027 A1 *   2/1998   ............. C07F/5/04

* cited by examiner

Primary Examiner—Wayne A. Langel
Assistant Examiner—Jonas N. Strickland
(74) Attorney, Agent, or Firm—Antonelli, Terry, Stout & Kraus, LLP

(57) ABSTRACT

The invention relates to the novel lithium bisoxalatoborate compound, and to a method for producing this compound, on the basis of a lithium compound, an oxalic acid or an oxalate, and a boron compound. The invention also relates to another production method on the basis of lithium boron hydride and oxalic acid, and to the use of lithium bisoxalatoborate as a conducting salt in lithium-ion batteries.

14 Claims, 1 Drawing Sheet

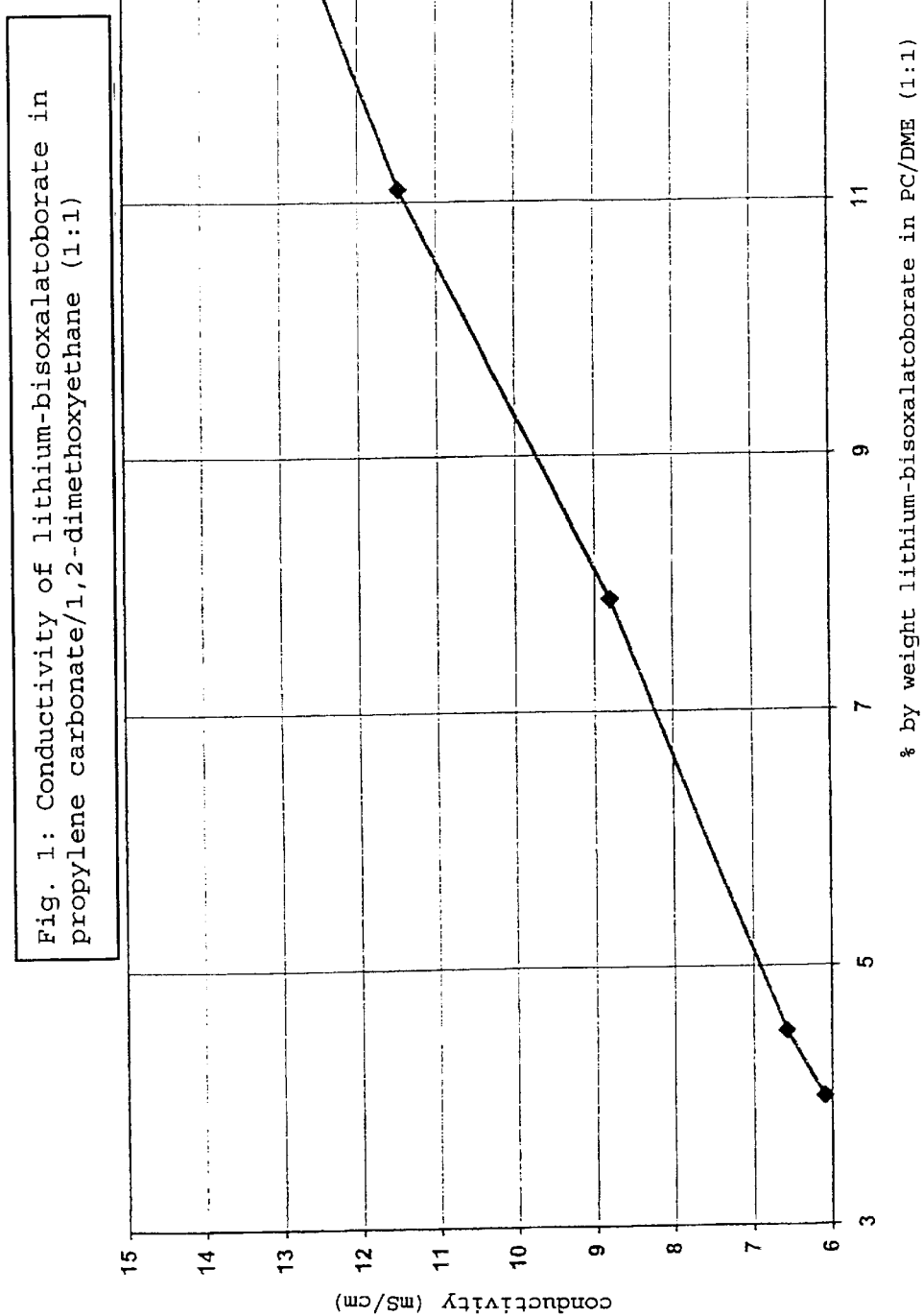
Fig. 1: Conductivity of lithium-bisoxalatoborate in propylene carbonate/1,2-dimethoxyethane (1:1)

LITHIUM BISOXALATOBORATE, THE PRODUCTION THEREOF AND ITS USE AS A CONDUCTING SALT

The subject matter of the invention is lithium-bisoxalatoborate, $Li[(C_2O_4)_2B]$, two methods for the production thereof, and the use of lithium-bisoxalatoborate as a conducting salt in lithium ion batteries.

At present, lithium hexafluorophosphate ($LiPF_6$) is used as a conducting salt in all commercial lithium ion batteries. This salt has the necessary prerequisites for use in high-energy cells, i.e. it is easily soluble in aprotic solvents, it leads to electrolytes having high conductivities, and it has a high level of electrochemical stability. Oxidative decomposition first occurs at potentials of >approximately 4.5V. $LiPF_6$, however, also has serious disadvantages, which are mainly to be attributed to its lack of thermal stability. In solution, a dissociation into LiF and $PF_5$ takes place, even if only slight, which can lead to a cationic polymerisation of the solvent, caused by the Lewis acid $PF_5$. Upon contact with moisture, caustic hydrofluoric acid is released, which, on the one hand makes handling more difficult, because of its toxicity and corrosiveness, and, on the other hand, can lead to the (partial) dissolution of the transition-metal oxides (for example $LiMn_2O_4$) used as cathode material. In this way, the cycle stability of the respective electrochemical energy store is affected.

With this background in mind, intensive efforts are being made with the aim of developing alternative conducting salts. As such, lithium salts with perfluorated organic radicals are being tested above all. In particular, lithium trifluoromethane sulphonate, lithium bis(trifluoromethane sulphonyl)imide and the lithium methides, the most fundamental of which is lithium bis(trifluoromethane sulphonyl) methide, are to be mentioned. These salts also have disadvantages, which hitherto prevented their use in commercial lithium batteries. The first-mentioned salt does not give the electrolytes produced with it a sufficiently high conductivity. The last-mentioned salts admittedly have a conductivity which is equal to that of $LiPF_6$, but because of the costly production methods are not of interest commercially. Additionally, the imide has a corrosive effect on aluminium sheets, which are used as current diverters in many battery systems. Apart from this, because of the high fluorine content of the compounds, under unfavourable conditions exothermal reactions with lithium are to be feared.

Lithium organoborates were tested as a further class of compound for use as a conducting salt. However, their use in lithium ion batteries was not seriously taken into consideration because of the low oxidation stability, the safety problems linked with the formation of triorganoboranes as well as their high price.

The lithium borate complex salts $[(R^1O)_2B(OR^2)_2]Li$ described in DE 19633027 A1 represent a substantial step forward. In this connection, $R^1$ and $R^2$ are the same or different, $R^1$ and $R^2$ are, if appropriate, connected to each other by a single bond or a double bond, $R^1$ and $R^2$ may be, individually or jointly, an aromatic ring from the group phenyl, naphthyl, anthracenyl or phenanthrenyl, which can be unsubstituted or substituted one to four times by A or Hal, Hal standing for fluorine or chlorine and A meaning alkyl with 1 to 8 C-atoms, which in turn can be halogenised one to four times.

A disadvantage of these compounds is, on the one hand, the stabilities of the non-fluorinated derivatives which, although improved, are in no way sufficient for the 3V systems required. Thus, for example, the unsubstituted lithium-bis[1,2-benzenediolato(2-)-O,O] borate(1-) decomposes when an anodic potential of 3.6 V is exceeded. This value lies clearly below that of the standard conducting salt $LiPF_6$ (approximately 4.5V). As a result of increasing fluorine substitution of the organic radical, the oxidation stability rises to a value of approximately 4V for the perfluorated compound. However, these values are still lower than in the case of the standard salt $LiPF_6$. The stability of the borates which are described, however, increases further because of a top layer formation during cyclisation, so that for some compounds almost sufficient stabilities are achieved. The stable compounds, however, have high molar masses (for example 378 g/mol for the perfluorated catecholate compound). Also, the preliminary stages required for the synthesis are not commercially available, but instead have to be produced in a costly way. Finally, compounds with CF bonds represent a potential safety risk, because they are not thermodynamically stable with respect to metallic lithium.

The underlying object of the invention is therefore to eliminate the disadvantages of the prior art and to develop an electrochemically stable lithium compound which has a good solubility in the aprotic solvents used by the battery industry, and also a method for the production thereof.

The object is achieved by the lithium compound lithium-bisoxalatoborate, $Li[(C_2O_4)_2B]$, indicated in claim 1. The independent claims 2 and 11 indicate two different methods for the production of lithium-bisoxalatoborate, claims 3 to 10 and 12 to 13 develop the method further and claim 14 indicates a use of the compound lithium-bisoxalatoborate.

Surprisingly, although it does not have any fluorine substituents, lithium-bis(oxalatoborate) has an excellent oxidation resistance. Thus, solutions of this salt in a mixture of ethylene carbonate (EC) and 1,2-dimethoxyethane (DME) are stable up to a voltage of 4.6V.

Furthermore, the conductivities which can be achieved with the salt in accordance with the invention are note worthy. Thus, a 0.56 m solution in a 1:1 mixture of EC and DME has a conductivity of 10.3 mS/cm at room temperature. In the usual solvent mixture propylene carbonate (PC)/DME (1:1), the conductivity of lithium-bisoxalatoborate in the case of different concentrations was measured (FIG. 1). It can be inferred from the measurement results that with concentrations of up to 15% by weight, conductivities of up to 14 mS/cm are achieved (see FIG. 1). These values are at the same level as, or even above, the conductivities which can be achieved with $LiPF_6$. Thus, for 1 m solutions of $LiPF_6$ in dimethyl carbonate (DMC)/EC, 11.0 mS/cm is achieved.

The molar mass of 193.8 g/mol is admittedly approximately 27% above that of the $LiPF_6$, but clearly below that of the borates described in DE 19633027 A1. This is not problematic, however, because electrolytes with lithium-bis(oxalatoborate) are also sufficiently conductive at lower concentrations (for example approximately 0.5 mol/l).

The lithium-bis(oxalatoborate) is easily soluble in water and in many polar aprotic solvents. In tetrahydrofuran (THF), approximately 42% by weight dissolves at 50° C. and approximately 30% by weight dissolves at 23° C. It has a solubility of at least 15% by weight in diethylene glycol dimethyl ether (diglyme) and mixtures of diglyme and carbonates.

According to thermogravimetry experiments, lithium-bis(oxalatoborate) is fully stable at up to approximately 300° C.

The lithium-bis(oxalatoborate) in accordance with the invention can be produced by reacting a lithium compound, such as lithium hydroxide (anhydrous or the hydrate) or lithium carbonate or a lithium alkoxide, with oxalic acid or an oxalate and a boron compound, such as boron oxide or boric acid or a boric acid ester.

The reaction can be carried out in a solvent, but does not necessarily have to be.

Preferably, lithium hydroxide or lithium carbonate is reacted with a stoichiometric amount of oxalic acid and a stoichiometric amount of boric acid or boron oxide in water, for example:

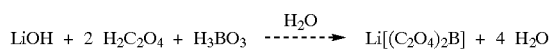

The reaction of lithium oxalate with oxalic acid and boric acid or boron oxide in water is also preferred, for example:

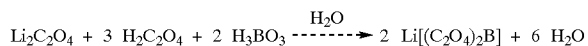

The sequence in which the components are added does not play a significant role. Preferably, oxalic acid is placed in an aqueous solution and the calculated amount of lithium base is added, or lithium oxalate is mixed with the 3-fold molar amount of oxalic acid. Subsequently, the calculated amount of boric acid or boron oxide is added to this partially neutralised oxalic acid solution.

The reaction temperature lies in the range between 0 and 100° C.

After the end of dosing, the mixture is heated to 50 to 100° C. for a time and the water is then distilled off. When crystallisation begins, the pressure is slowly lowered. The final drying takes place whilst stirring, at approximately 50 to 150° C. and <approximately 1 mbar.

A solid product is obtainable which is partially lumpy, granular or fine-crystalline solid depending on the drying unit which is selected.

In a variant of the production method in accordance with the invention, water is not necessarily added as the solvent. However, water forms as a reaction by-product in different amounts. According to this variant of the method, it is provided that the starting materials are suspended in an organic solvent and the water which is released during the formation reaction is removed by azeotropic distillation. All solvents which cannot be mixed with water or which can be mixed therewith to a limited extent, which form a water/solvent azeotrope and have such a high volatility that a subsequent product drying is possible, are suitable for this process. Depending on the temperature and stirring conditions selected, the reaction starts spontaneously or is initiated by the addition of small amounts of water. The reaction temperature of the exothermic reaction lies between 0 and 150° C. The reaction mixture is subsequently heated to boiling temperature, the water of crystallisation and reaction water being removed by azeotropic distillation. Aromatic substances, such as benzene, toluene, xylene and ethyl benzene, are particularly suitable for the course of the reaction and the azeotropic dehydration. Thus, for example, when toluene is used, the calculated amount of water can be precipitated within a reaction of time of approximately 2 to 4 hours.

The product in accordance with the invention precipitates in fine-crystalline, free-flowing form, completely anhydrous and with good purity. It is separated from the reaction solvent by filtration, washed with an aprotic solvent (for example toluene or comparatively volatile hydrocarbons, such as hexane or pentane) and dried in a vacuum and/or at comparatively high temperatures (50 to 150° C.).

Ethers which cannot be mixed with water, such as 2-methyl tetrahydrofuran, for example, are also suitable to a limited extent. In ethereal solvents, however, the lithium-bisoxalatoborate is only formed in impure form, i.e. it subsequently has to be purified in a relatively costly way by fractional crystallisation.

According to a further embodiment of the method in accordance with the invention, the product in accordance with the invention can also be obtained starting from lithium alkoxides LiOR and boric acid esters $B(OR)_3$ (with R=methyl, ethyl). In order to do this, a lithium alkoxide is mixed with a boric acid ester, the corresponding lithium tetraalkoxy borate $Li[B(OR)_4]$ presumably being formed. This reaction does not necessarily require a solvent, but can be carried out in the presence of a solvent. The reaction mixture is subsequently reacted with oxalic acid and the alcohol component which is released is removed by distillation. Ideally, those boric acid esters which release as much volatile alcohols as possible are taken for this variant, i.e. the methyl compound or ethyl compound:

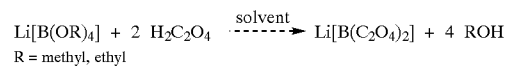
R = methyl, ethyl

The alcohol itself (i.e. methanol or ethanol) or an aprotic solvent, such as acetonitrile, can be used as the solvent. In this variant of the method, the reaction temperature amounts to 0 to 100° C., the range between approximately 20 and 70° C. being most suitable. When acetonitrile is used, then, after distillation of the alcohol which is released at normal or reduced pressure, the product in accordance with the invention precipitates upon cooling, in the form of colourless crystals, which can be filtered off and cleaned by washing with acetonitrile or another volatile, aprotic solvent (for example hexane, pentane, diethyl ether).

In accordance with a further variant of the method, $LiBO_2$ as both lithium compound and boron compound can be reacted together with oxalic acid to form the desired product:

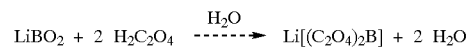

In accordance with a further production method in accordance with the invention, lithium-bis(oxalatoborate) can also be prepared in aprotic media directly in fully anhydrous form. In order to do this, lithium boro-hydride is reacted in a solvent in accordance with the following reaction equation with two equivalents of anhydrous oxalic acid:

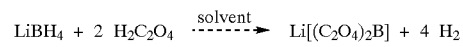

The reaction is advantageously carried out in a solvent in which $LiBH_4$ has a certain solubility, for example in ethers such as tetrahydrofuran (THF). Particularly advantageously, those solvents which are commonly used by the battery industry for the production of electrolytes are also used. In particular, polyethers, such as 1,2-dimethoxyethane, are suitable. The reaction temperature is not of crucial importance. It is limited downwards by the viscosity, which rises as the temperature falls. On the other hand, however, it should not rise too high, in order to avoid a reductive attack, possible in principle, of the hydride on the oxalic acid or lithium-bis(oxalatoborate). In general, the temperature range between 20 and 50° C. is most suitable. The course of the reaction can be followed simply by observing the formation of gas.

In the following examples, the subject-matter of the invention is explained in greater detail.

EXAMPLE 1

Synthesis of Li[$(C_2O_4)_2$B] from lithium hydroxide, oxalic acid and boric acid in water with subsequent total evaporation.

252.14 g (2.00 mol) oxalic acid dihydrate and 23.94 g (1.00 mol) calcined LiOH were dissolved in 1500 g distilled water. The temperature rose to approximately 30° C. and a clear solution formed as a result of the heat of neutralisation. Within 15 minutes, a solution of 61.83 g (1 mol) boric acid in 1300 g water was then added (no visible exothermy). The solution was then concentrated by distillation at normal pressure. Within approximately 3 hours, 2165 g water were distilled off. The bottom temperature thereby rose to 104.2° C.; crystals precipitated out of the colourless solution. A further 450 g water were distilled off, and the remaining suspension (411 g) was placed in a porcelain cup and put in a vacuum shelf dryer for complete evaporation. After vacuum drying for 24 hours at 100° C., 184.8 g (95% yield) of a colourless granulate were obtained.

|  | found | | theory | |
| --- | --- | --- | --- | --- |
|  | % | mol, normalised to B = 1 | % | mol, normalised to B = 1 |
| Li | 3.68 | 1.06 | 3.58 | 1 |
| B | 5.4 | 1.00 | 5.58 | 1 |
| $C_2O_4$ | 85.6 | 1.95 | 90.8 | 2 |

NMR data:
$\delta^{11}$B (THF/$C_6D_6$): 7.70 ppm $h_{1/2}$ = 28 Hz
$\delta^{13}$C (THF/$C_6D_6$): 159.1 ppm

EXAMPLE 2

Synthesis of Li[$(C_2O_4)_2$B] from lithium carbonate, oxalic acid and boric acid in toluene with subsequent azeotropic water separation.

126.07 g of oxalic acid dihydrate (1.00 mol) and 30.98 g of (0.500 mol) 99.8% boric acid were suspended in 600 ml toluene in a 2 l four-necked flask with thermometer, Teflon-blade stirrer and water separator. After heating to 60° C., first of all approximately 5 g of $Li_2CO_3$ were added using a solids dosing bulb. Within half an hour, no significant formation of gas could be established. Thereupon, 3.63 g of $H_2O$ were added with a syringe. The reaction now began immediately, with strong formation of gas (2 l in 5 minutes). Within 5 minutes, the remaining amount of $Li_2CO_3$ (in total 18.50 g≙0.250 mol) was added. 6.19 l of gas (≙251 mmol, 100%) were thereby formed. The reaction mixture was then heated to boiling point and refluxed for 4 hours. Already after 20 minutes, 57.3 g of water (≙81% of the theoretically expected amount) had precipitated. Because the solid was baking strongly, it was cooled briefly and the reaction mass was scraped off the flask wall with a spatula. After 4 hours of refluxing, no more water precipitated (in total 72.0 g≙101% of the theoretically expected amount); the yellowish suspension was cooled and filtered using a glass frit. The cream-coloured, fine-crystalline sediment was washed twice with hexane and first dried at room temperature to constant weight (97.4 g≙100.5% of the theoretical yield). As result of vacuum drying for 4 hours at 90° C., 0.2 of residual moisture was removed.

Analysis:

NMR data: $\delta^{11}$B (THF/$C_6D_6$): 7.70 ppm

EXAMPLE 3

Synthesis of Li[$(C_2O_4)_2$B] from lithium hydroxide, oxalic acid and boric acid in toluene with subsequent azeotropic water separation.

8.70 g (125 mmol) of $B_2O_3$ (dried at 300° C. in a drying pistol) and 63.04 g of (500 mmol) oxalic acid dihydrate were suspended in 300 ml of toluene in a 500 ml four-necked flask with KPG stirrer, water separator and thermometer. With the addition of 10.37 g (250 mmol) LiOH.$H_2O$, the temperature rose spontaneously to 39° C. The azeotropic water separation began immediately after the boiling point was reached, and within 160 minutes delivered 30.2 g of water (≙96% of the theoretically expected amount). Because the reaction product stuck to the flask wall, it was twice cooled slightly and the product was scraped off with a spatula.

Yield: 49.9 g of beige powder≙103% of the theoretical yield.

EXAMPLE 4

Synthesis of Li[$(C_2O_4)_2$B] from lithium carbonate, oxalic acid and boric acid in 2-methyl tetrahydrofuran (2-MeTHF) with subsequent azeotropic water separation.

252.14 g of oxalic acid dihydrate (2.00 mol) and 61.83 g of boric acid (1.00 mol) were suspended in approximately 0.8 l of 2-MeTHF and heated to 40° C. in the same apparatus as in Example 2. 36.95 g (0.50 mol) of $Li_2CO_3$ were then added in small amounts. To accelerate the reaction, 2×1.5 ml water was sprayed in. The formation of gas took place relatively evenly and produced approximately 255 mmol within one hour. Refluxing was carried out thereupon, for 13 hours. After 5 hours, the theoretically expected amount of gas had escaped; the solution was intensely yellow in colour and a total of 120.6 g of 2-MeTHF-saturated water precipitated in the water separator (≙114.2 g of pure water≙83% of the theoretically expected amount). After 14 hours' reaction time, the yellow suspension was cooled and filtered by way of a G3-frit.

Analysis of the filtrate:

Filtrate: 1221 g, intensely yellow

| NMR data: $\delta^{11}$B (2-MeTHF/THF): | 20.4 ppm $h_{1/2}$ = 205 Hz | 24% |
| --- | --- | --- |
| | 7.66 ppm Li [$(C_2O_4)_2$B] | 65% |
| | 5.25 ppm $h_{1/2}$ = 72 Hz | 11% |

The product was subsequently freed from the solvent and crystallised out of THF/diethyl ether.

Yield: 83.3 g≙43% of the theoretical yield

Analysis of the product: the crystallisate dissolved in THF now only shows the $^{11}$B-NMR-signal at 7.7 ppm

EXAMPLE 5

Synthesis of Li[$(C_2O_4)_2$B] from lithium methoxide, oxalic acid and trimethyl borate in methanol.

4.97 g of (131 mmol) lithium methoxide were dissolved in 119 g of methanol, and at 30° C., within 10 minutes, and there was mixing with a solution of 13.51 g of (130 mmol) trimethyl borate in 30 g of methanol. The internal temperature thereby rose to 37° C.; the reaction solution was clear and colourless. 23.40 g (260 mmol) of anhydrous oxalic acid were added to this solution all at once. The reaction mixture thereupon briefly turned curd-like (approximately 10 seconds), in order then to turn into a slightly viscous, milky suspension. No exothermy could be established. The reaction mixture was boiled at reflux (66.6° C.) for 45 minutes and, after cooling, was decanted from an extremely finely dispersed soft solid (the solid could not be separated with a G 3 g lass frit). The total evaporation of the clear decanted solution on the rotation evaporator produced 23.71 g of a greasy solid. Taking into account the decantation loss, this corresponds to 25.4 g≙101% of the theoretical yield. In the rotation evaporator, small amounts of a colourless sublimate were observed, which did not produce a $^{11}$B-NMR signal and dissolved in water with an acidic reaction, which points to oxalic acid. The soft drying residue was not completely soluble in THF. The THF-soluble portion, however, only showed a $^{11}$B-NMR signal at 7.7 ppm, which comes from Li[$(C_2O_4)_2$B]. The residue was digested with the approximately 6-fold amount of THF, filtered and evaporated. During evaporation, a greasy product resulted, which became increasingly dark in colour. After separation of the solvent, a colourless solid began to sublime off.

Yield (partly oily): 16.8 g (≙67% raw product)

The raw product was subsequently cleaned by recrystallisation out from THF/diethyl ether.

Yield: 10.2 g≙40% of the theoretical yield.

EXAMPLE 6

Synthesis of Li[$(C_2O_4)_2$B] from LiBH$_4$ and oxalic acid in THF.

68.06 g (0.756 mol) of oxalic acid, dried at 120° C. for two hours, were dissolved in 120 g of THF and cooled to −5° C. in a 0.5 l double-casing reactor. A solution of 8.10 g of LiBH$_4$ (0.372 mol) in 49.2 g of THF was added to this solution within 70 minutes. 22.6 l of gas (0.93 mol≙63% of the theoretically expected amount) were thereby given off. It was then quickly heated to boiling point. Approximately a further 8 l of gas thereby escaped. After 45 minutes' boiling at reflux (66° C.), it was cooled to 24° C., a sample was taken and 3.3 g of LiH were added. 2.81 l of gas (≙116 mmol) were given off. The suspension was filtered, with 300.3 g of clear filtrate precipitating. The filtrate was then evaporated on the rotation evaporator to constant weight. 47.6 g (66% of the theoretical yield) of a white powder were obtained, which for the purpose of purification still had to be recrystallised.

Analysis:

NMR data:

$\delta^{11}$B (sample before lH addition): 9.7 ppm (32%); 7.7 ppm (68%)

$\delta^{11}$B (filtrate before evaporation): 9.7 ppm (7%); 7.7 ppm (88%); 5.2 ppm (5%)

What is claimed is:

1. Lithium-bisoxalatoborate, Li[$(C_2O_4)_2$B].

2. Method for producing lithium-bisoxalatoborate, Li[$(C_2O_4)_2$B], wherein a lithium compound is reacted with oxalic acid or an oxalate and with a boron compound.

3. Method according to claim 2, wherein the reaction is carried out in a solvent.

4. Method according to one of claim 3, wherein the solvent is water or an alcohol with 1 to 5 C atoms or an organic solvent which cannot be mixed with water or can be mixed therewith to a limited extent and which forms an azeotrope with water.

5. Method according to claim 3, wherein lithium hydroxide or lithium carbonate or lithium oxalate is reacted with oxalic acid and boric acid or boron oxide in the ratio Li$^+$:oxalate:B$^{3+}$=1:2:1 and in the presence of water.

6. Method according to claim 3, wherein lithium hydroxide or lithium carbonate or lithium oxalate is reacted with oxalic acid and boric acid or boron oxide in the ratio Li$^+$:oxalate:B$^{3+}$=1:2:1, an organic solvent which forms an azeotrope with water is added to the water-containing reaction mixture and the water is removed azeotropically.

7. Method according to claim 6, wherein the organic solvent which forms an azeotrope with water is benzene, toluene, xylene or ethyl benzene.

8. Method according to claim 2, wherein the lithium compound is LiOH or LiOH.H$_2$O or Li$_2$CO$_3$ or lithium oxalate or LiOR, wherein R is methyl or ethyl.

9. Method according to one of claim 2, wherein the boron compound is boron oxide B$_2$O$_3$ or boric acid H$_3$BO$_3$ or a boric acid ester B(OR)$_3$ wherein R is methyl or ethyl.

10. Method according to one of claim 2, wherein LiBO$_2$ is used as the lithium and boron compound.

11. Method for producing lithium-bisoxalatoborate, Li[$(C_2O_4)_2$B], wherein LiBH$_4$ is reacted with oxalic acid in an aprotic solvent.

12. Method according to claim 11, wherein the aprotic solvent is an ether or a polyether.

13. Method according to claim 12, the ether is tetrahydrofuran (THF) or the polyether is 1,2-dimethoxyethane.

14. In a lithium battery, the improvement comprising the use of lithium-bisoxalatoborate, Li[$(C_2O_4)_2$B], as a conducting salt in lithium batteries.

* * * * *